United States Patent [19]

Warriner

[11] Plant 4,843

[45] May 4, 1982

[54] ROSE PLANT 72-2461

[75] Inventor: William A. Warriner, Tustin, Calif.

[73] Assignee: Jackson & Perkins Company, Medford, Oreg.

[21] Appl. No.: 189,816

[22] Filed: Sep. 22, 1980

[51] Int. Cl.[3] ..... A01H 5/00

[52] U.S. Cl. ..... Plt./19

[58] Field of Search ..... Plt./19–20

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having near red, exhibition style blooms. The blooms having little fragrance and growing on a vigorous upright plant.

1 Drawing Figure

This present invention relates to a new and distinct variety of rose plant of the hybrid tea class which was originated by me by crossing the variety Billionaire, U.S. Plant Pat. No. 3,381, with an unnamed variety.

The primary objective of this breeding was to produce a new rose variety combining the plant characteristics of the variety Billionaire with flower type of the unnamed variety and with a color near that of Billionaire. This objective was substantially achieved along with other desirable improvements as evidenced by the following unique combination of characteristics which are outstanding in the new variety and which distinguish it from its parents as well as from all other varieties of which I am aware:

1. A vigorous, upright plant habit.
2. Bud color near red, corresponding to RHS 46A.
3. Open flower color close to RHS 47A.
4. A type of bud form usually considered to be of exhibition quality.
5. Very little fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Billionaire, U.S. Plant Pat. No. 3,381.

*Pollen parent.*—Unnamed variety.

Classification:

*Botanical.*—Rosa hybrid.

*Commercial.*—Hybrid tea.

FLOWER

Observations made from specimens grown at Irvine, Calif. in August, 1980.

Blooming habit: Continuous.

Bud:

*Size.*—$1\frac{1}{4}''$ to $1\frac{1}{2}''$ when petals start to unfurl.

*Form.*—Short, blunt top.

*Color.*—When sepals first divide, Red 46A; when sepals fully open, Red 46B. When half blown; upper side of petals, Red 47A changing quickly to 47B; lower side of petals Red 47A.

*Sepals.*—Color: outer surface Green 138A with some browning occurring upon ageing. Few stipitate glands on surface. Three appendaged sepals normally appendaged; two unappendaged sepals hairy edged.

*Receptacle.*—Color: Green 138A. Shape: funnel. Size: large, long. Surface: smooth.

*Peduncle.*—Length: short. Surface: occasionally prickly. Color: light green. Strength: stiff, erect.

*Opening.*—Spiral fashion.

Bloom:

*Size.*—Large. Average open size is 5 inches.

*Borne.*—Singly, sometimes several together.

*Stems.*—Long, strong.

*Form.*—When first open, high centered. Permanence: retains its form to the end, outer petal edges slightly curled.

*Petalage.*—Number of petals under normal conditions, 35.

*Color.*—Center of flower: upper side of petals, Red 47B; reverse side of petals, Red 47A; base of petals, small area of yellow. General tonality from a distance, Red 47B.

*Variegations.*—Sometimes a green foliaceous area on one or two outer petals.

*Discoloration.*—General tonality at third day, lightens to 47C and 47D.

*Fragrance.*—None.

Petals:

*Texture.*—Thick.

*Shape.*—Round.

*Form.*—Tips slightly recurved.

*Arrangement.*—Informal. Petaloids in center, few.

*Persistence.*—Drop off cleanly.

*Lastingness.*—On the plant, long. As cut flower, long.

Reproductive parts:

*Anthers.*—Large, many. Color: orange-yellow, reddish brown in area of midrib. Arrangement, regular around styles.

*Filaments.*—Color: reddish brown with yellow base.

*Pollen.*—Gold yellow.

*Styles.*—Color: red/purple.

*Stigmas.*—Color: yellow.

PLANT

Form: Bush.

Growth: Very vigorous, upright.

Foliage: Number of leaflets on normal mid-stem leaves, 7.

*Size.*—Large.

*Quantity.*—Normal.

*Color.*—New foliage: red-purple near 59A. Old foliage: normal medium green.

Leaflets:

*Shape.*—Oval pointed.

*Texture.*—Upper side: leathery.

*Edge.*—Serrated.

*Serration.*—Single, small.

*Petiole.*—Rachis: color: reddish. Underside: prickles.

*Stipules.*—Long, bearded.

*Disease resistance.*—Normally resistant to mildew under normal growing conditions at Irvine, Calif.

Wood:

*New wood.*—Color: light green. Bark: smooth.

*Old wood.*—Color: green. Bark: smooth.

Prickles:

*Quantity.*—On main stalks, many. On laterals from stalks, many.

*Form.*—Long base, medium, hooked downward.

*Color when young.*—Brown.

*Position.*—Irregular.

Small prickles:

*Quantity.*—On main stalks, few. On laterals, few.

*Color.*—Brown.

I claim:

1. A new and distinct variety of rose plant of the hybrid tea class, substantially as herein shown and described, characterized particularly as to novelty by the unique combination of its exhibition style flower form of light red, little fragrance on a vigorous upright hybrid tea plant.

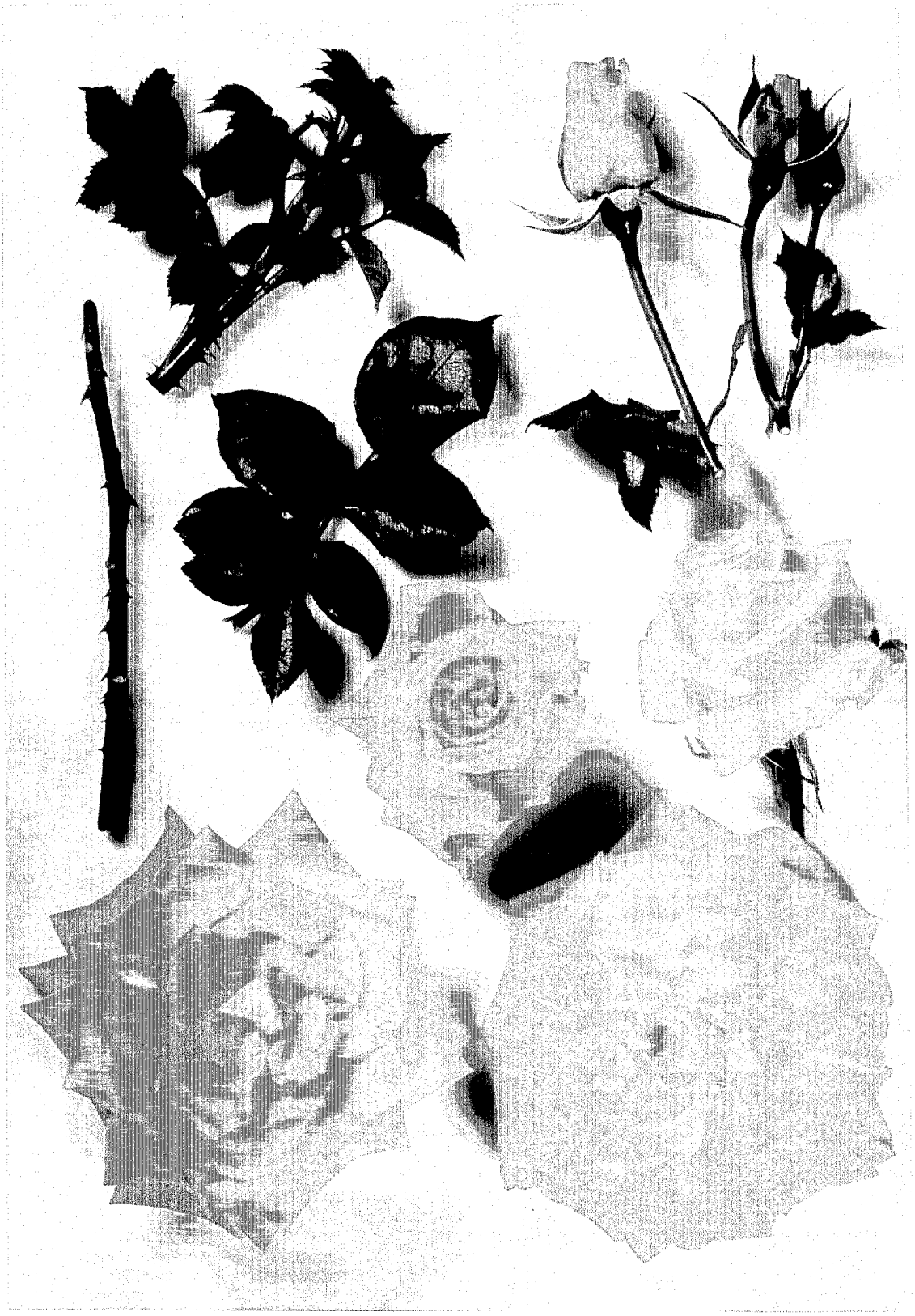

* * * * *